United States Patent
Nishibe et al.

(10) Patent No.: US 6,737,085 B2
(45) Date of Patent: May 18, 2004

(54) APOCYNUM VENETUM EXTRACT FOR USE AS ANTIDEPRESSANT

(75) Inventors: Sansei Nishibe, Hokkaido (JP); Tsutomu Sasaki, Chiba (JP); Shujiro Seo, Chiba (JP); Veronika Butterweck, Müenster (DE)

(73) Assignee: Tokiwa Phytochemical Co., Ltd., Sakura (JP)

(*) Notice: Subject to any disclaimer, the term of this patent is extended or adjusted under 35 U.S.C. 154(b) by 0 days.

(21) Appl. No.: 09/985,165

(22) Filed: Nov. 1, 2001

(65) Prior Publication Data
US 2002/0090403 A1 Jul. 11, 2002

(30) Foreign Application Priority Data
Nov. 1, 2000 (JP) .......................... 2000-334122

(51) Int. Cl.$^7$ .......................... A23L 1/28; A61K 33/00; A61K 47/00; B09B 3/00
(52) U.S. Cl. .......................... 424/725; 424/439; 426/655
(58) Field of Search .......................... 424/439, 725, 424/774; 426/655; 435/410

(56) References Cited

U.S. PATENT DOCUMENTS 5,919,460 A * 7/1999 Ingram .................... 424/195.1
6,416,807 B1 * 7/2002 Yamamoto ................ 426/597

FOREIGN PATENT DOCUMENTS

JP 9-224623 9/1987
JP 10-167978 6/1998

OTHER PUBLICATIONS

Nishibe et al., Studies on the constituents of Chinese medicine . . . , 1993, Japanese J. of Pharmacognosy, abstract only.*
Xiong et al., Hepatoproctective effect of Apocynum venetum and its active constiuents, Mar., 2000, Planta Medica, vol. 66, No. 2, pp. 127–133.*
Linde, Klaus et al., British Medical Journal, vol. 313, pp. 253–258, 1996.
Bove, Geoffrey, The Lancet, vol. 352, pp. 1121–1122 (1998).
Fugh–Berman, Adriane, The Lancet, vol. 355, pp. 134–138, 2000.
Moore, Linda B. et al., Proc. Natl. Acad. Sci. USA, vol. 97, No. 13, pp. 7500–7502.
Porsolt, R.D. et al., Nature, vol. 266, pp. 730–732, 1977.
Butterweck, Veronika et al., Planta Medica 66, pp. 3–6, 2000.
Deutsche Apotheker Zeitung, vol. 127, No. 23, pp. 1227–1230, 1987.

* cited by examiner

Primary Examiner—David M. Naff
Assistant Examiner—Deborah K. Ware
(74) Attorney, Agent, or Firm—Birch, Stewart, Kolasch & Birch, LLP

(57) ABSTRACT

The present invention provides (1) an Apocynum extract containing not less than 4% of flavonoid compounds and is free of hypericin and hyperforin, (2) an antidepressant composition (in the form of a food, dietary supplement or medicine) containing the Apocynum extract, and (3) a method for treating depression using the Apocynum extract.

8 Claims, No Drawings

APOCYNUM VENETUM EXTRACT FOR USE AS ANTIDEPRESSANT

BACKGROUND OF THE INVENTION

The present invention relates to novel Apocynum extracts, antidepressant compositions containing the Apocynum extracts in the form of foods, dietary supplements, medicines and the like, and methods for treating depression using the Apocynum extracts.

The etiology of depression has been extensively discussed by many works, but has not been sufficiently explained yet. Various factors seem to be involved in the etiology and complicated with each other. Possible factors include biological factors such as neurochemical and genetic findings as well as situational or psychosociological factors such as previous personality or life stress.

Clinical features of depression include depressive state, anhedonia (the inability to enjoy themselves), psychomotor inhibition, incoherence of thought/cognition, anxiety and agitation, physical (autonomic) symptoms, etc.

Currently available drugs for treating depression (antidepressants) include tricyclic antidepressants such as imipramine, clomipramine, trimipramine; tetracyclic antidepressants such as maprotiline, mianserin; triazolopyridines such as trazodone; benzketoxime-based selective serotonin reuptake inhibitors such as fluvoxamine. However, tricyclic or similar cyclic antidepressants have been shown to have side effects such as anticholinergic effects (dry mouth, blurred near vision, constipation, dysuria), antihistamine effects (weight gain, sedation), antiadrenergic effects (postural hypotension, vertigo, dizziness) and cardiotoxicosis or acute poisoning caused by excessive intake. Selective serotonin reuptake inhibitors have been associated with the danger of inducing serotonin syndrome. Therefore, there is a demand for antidepressants with less side effects.

Recently, St. John's Wort was reported to be effective in treating depression (K. Lindle et al., British Medical Journal, 313, 253 (1996)). St. John's Wort or *Hypericum perforatum* is provided by drying aerial parts harvested during the flowering stage, and has been long used as extracted oil in Europe for treating wound and neuralgia. Moreover, flavonoid compounds such as hyperoside and isoquercitrin contained in St. John's Wort were shown to have an antidepressant effect (V. Butterweck, et al., Planta Med. 66, 3–6 (2000)).

However, St. John's Wort contains a compound having a dimer structure of anthraquinone called hypericin, which is known to cause photosensitivity as one of serious side effects (B. Geoffrey, Lancet (North American Edition), 352, 1121–1122, (1998)). A component of St. John's Wort, hyperforin is also known to induce a drug metabolizing enzyme to affect pharmacokinetics of drugs such as cyclosporin (F. -B. Adriane, Lancet, 355, 9198, 134–138, (2000), L. B. Moore et al., Proc. Natl. Acad. USA, 97, 7500–7502, (2000)).

In China, leaves of *Apocynum venetum* L. are used as substitute tea, which is effective in lowering fever or treating hypertension, cardiac insufficiency, bronchitis, dropsy, neurasthenia, etc.

Recently, roasted tea of leaves of *Apocynum venetum* L. (Apocynum tea) was reported to show a cholesterol-lowering effect (see Japanese Unexamined Patent Publication No. 9-224623) and prophylactic/curing effects against infective diseases (see Japanese Unexamined Patent Publication No. 10-167978). However, these teas or hot water extracts of *Apocynum venetum* L. normally contain 1–2% flavonoids but never contain more than 4% flavonoid compounds. No extracts of *Apocynum venetum* L. containing 4% or more flavonoid compounds have been reported.

Moreover, nobody has known that *Apocynum venetum* L., teas of *Apocynum venetum* L. and extracts of *Apocynum venetum* L have an antidepressant effect.

An object of the present invention is to provide a naturally derived antidepressant composition in the form of a food, dietary supplement, medicine or the like that contains neither hypericin nor hyperforin and is safer even during extended administration, as well as a method for treating depression using it.

SUMMARY OF THE INVENTION

After extensive studies to find a safer antidepressant, we succeeded in preparing a new extract of leaves of *Apocynum venetum* L. containing 4% or more of flavonoid compounds and accomplished the present invention on the basis of the finding that this extract shows an antidepressant effect.

Accordingly, the present invention provides an Apocynum extract containing 4% or more of flavonoid compounds.

The present invention also provides an antidepressant composition containing the Apocynum extract. The composition may be in the form of a food, dietary supplement or medicine.

The present invention also provides a method for treating depression using the Apocynum extract.

THE MOST PREFERRED EMBODIMENTS OF THE INVENTION (1) Apocynum extracts

Leaves of *Apocynum venetum* L. (scientific name) are used. Leaves of *Apocynum venetum* L. may be used as fresh leaves as harvested or after dried or roasted, but preferably dried and roasted.

Apocynum extracts used in the present invention can be obtained by extracting leaves of *Apocynum venetum* L. with water, ethanol, ethanol hydrate or an organic solvent followed by concentration, optionally adsorbing thus obtained extract to an acrylic, styrene, methacrylic or aromatic synthetic adsorbent and concentrating fractions eluted with 10–95% ethanol hydrate, and optionally drying the extract, provided that they contain 4% or more of flavonoid compounds. The content of flavonoid compounds in the extracts is preferably 4–50%, more preferably 4–10%.

As used herein, flavonoid compounds mean materials in which two phenyl groups are linked via three carbon atoms of a pyran ring or a similar structure, including chalcone, flavanone, flavone, flavonol, flavanonol, flavanol (catechin), isoflavone and anthocyan.

Apocynum extracts of the present invention preferably contain 4% or more of flavonoid compounds as expressed in the total content of hyperoside and isoquercitrin. Apocynum extracts of the present invention also preferably contain 4% or more of flavonoid compounds as expressed in the total content of hyperoside, isoquercitrin, astragalin and trifolin. All these compounds are flavonol glycosides.

The content of flavonoid compounds in Apocynum extracts can be analyzed by high performance liquid chromatography, for example, and spectrophotometrically determined in a range of 280–340 nm.

Apocynum extracts of the present invention contain neither hypericin nor hyperforin. Hyperforin and hypericin in Apocynum extracts can be analyzed by using a high performance liquid chromatograph (Von J. Holzl and E. Ostrowski, Deutche Apotecker Zeit, 127, 1227–30 (1987)) on a column YMC PAK ODS 100×6 mm i.d. with a mobile phase consisting of acetonitrile:methanol:water:phosphoric acid=55:45:1:0.1 at 1 mL/min, during which a hyperforin peak appears at 8.9 min as monitored at a detection wavelength of 254 nm and a hypericin peak appears at 14.3 min as monitored at a detection wavelength of 590 nm. Apocynum extracts of the present invention show no peak corresponding to hypericin and hyperforin.

(2) Compositions

The present invention also provides antidepressant compositions containing Apocynum extracts in the form of a food, dietary supplement or medicine. Apocynum extracts used in the present invention preferably contain 4% or more of flavonoid compounds as determined above, though lower contents may also be suitable.

When compositions of the present invention are pharmaceutical compositions, the administration route is not specifically limited, but they preferably have a dosage form suitable for oral administration. Pharmaceutical compositions of the present invention can be in various dosage forms. For example, dosage forms suitable for oral administration include, but not limited to, tablets, capsules, powders, granules, pills, liquids, emulsions, suspensions, solutions, spirits, syrups, extracts and elixirs. Formulations may contain various pharmaceutically acceptable carriers including, but not limited to, excipients, binders, disintegrating agents, lubricants, flavors, colorants, sweeteners, corrigents, solubilizing agents, suspending agents, emulsifiers, coating agents, vitamin C and antioxidants.

The dose of pharmaceutical compositions of the present invention is generally 1 mg–2000 mg, preferably 1 mg–1000 mg daily per adult expressed as Apocynum extracts or 0.01 mg–300 mg expressed as total flavonoids. Obviously, the dose can be specifically adapted to the age, weight and condition of the patient being treated, the route and period of administration, the treatment progress and other factors. The daily dose can be divided into several subdoses. Compositions may be administered in combination with other antidepressants or other therapies.

Compositions of the present invention can be in the form of a food or dietary supplement. For example, Apocynum extracts can be mixed with base materials into noodles, breads, candies, jellies, cookies, soups and healthy beverages. These foods or dietary supplements can contain inorganic ingredients such as iron or calcium; various vitamins; oligosaccharides; dietary fibers such as chitosan; proteins such as soybean extracts; fats such as lecithin; and sugars such as sucrose or lactose, in addition to Apocynum extracts.

Apocynum extracts of the present invention can be combined with ginseng extracts, ginkgo leave extracts, Gotu-Kola extracts, Siberian ginseng extracts, astragalus extracts, guarana extracts, maca extracts, dandelion extracts, artichoke extracts, gentiana extracts, schisandra extracts to provide compositions in the form of a food, dietary supplement, medicine or the like having the effect of improving depression caused by mental stress.

Apocynum extracts of the present invention can be combined with extracts of black cohosh extracts, pumpkin seed extracts, soybean extracts, licorice extracts, Dong Quai extracts, chaste tree extracts, pomegranate extracts, and dioscorea extracts to provide compositions in the form of a food, dietary supplement, medicine or the like having the effect of improving climacteric melancholia.

(3) Depression

As used herein, depression refers to the disease classified as "depressions—related disorders in the International Classification of Diseases, Injuries and Causes of Death. $10^{th}$ version, ICD-10 published by World Health Organization or the disease evaluated as "depression" by multiaxial diagnosis according to DSM-IV of "Diagnostic Statistic Manual of Mental Disorders, DSM" published by American Psychiatric Association (APA) among various typing and classification protocols of depression so far proposed.

Thus, the term "antidepressant" means reducing, improving or preventing some symptoms of depression as defined above. Whether or not a composition is "antidepressant" can be determined by the patient's own feeling of improvement, some effect ascertained by the physician's diagnosis or the like.

(4) Effects

Apocynum extracts of the present invention were tested for antidepressant effect by a common method for evaluating antidepressant effect called as the forced swimming test (Porsolt et al., Nature, 266, 730–732 (1977)). As a result, Apocynum extracts showed an antidepressant effect comparable to a known tricyclic antidepressant imipramine-HCl.

The following examples further illustrate the present invention without, however, limiting the invention thereto. Various changes and modifications can be made by those skilled in the art and these changes and modifications are also included in the present invention.

EXAMPLES

Example 1

Preparation of Apocynum Extract (1)

Dried leaves of *Apocynum venetum* L. were ground by a laboratory mixer, and 1 kg of the ground leaves were combined with 6 liters of 70% ethanol and heated under reflux for two hours, and then filtered to give an extract. The residue was again heated under reflux for two hours with 6 liters of 70% ethanol, and then filtered to give an extract. The first and second extracts were combined and concentrated at 60° C. under reduced pressure to approximately 1/10 of the original volume, and then dried at 60° C. overnight under reduced pressure to give 290 g of a solid. The contents of hyperoside and isoquercitrin in this solid were determined by high performance liquid chromatography using a Waters 600E multisolvent delivery system and a Waters 2487 dual $\lambda$UV/VIS detector on an analytical column SHISEIDO CAPCELL PAK C18 (UG) 4.6 mm i.d.×150 mm at a detection wavelength of 330 nm with a mobile phase consisting of 0.1% aqueous trifluoroacetic acid:0.1% trifluoroacetic acid 50% acetonitrile in water=85:15 at a flow rate of 1.0 ml/min to show that the hyperoside content was 0.8% and the isoquercitrin content was 0.9%.

Example 2

Preparation of Apocynum Extract (2)

The extract obtained in Example 1 was condensed to approximately 1/20 of the original volume, then suspended in 2-fold excess of water and then adjusted to pH 3 with sulfuric acid and body fed with diatomaceous earth. This solution was poured onto a filter paper covered with diatomaceous earth to filter off insoluble matters. The filtrate was passed through 1 L of a synthetic adsorbent resin HP20 (Mitsubishi Chemical Corporation) to adsorb active components, and then washed with 2 liters of water to remove sugars or the like. Then, the filtrate was extracted with 2 liters of 70% ethanol to collect fractions containing active components, which were concentrated at 60° C. under reduced pressure to approximately 1/10 of the original volume, and then dried at 80° C. overnight under reduced pressure to give 95 g of a solid. The contents of hyperoside and isoquercitrin in this solid were determined by high performance liquid chromatography using a Waters 600E multisolvent delivery system and a Waters 2487 dual λUV/VIS detector on an analytical column SHISEIDO CAP-CELL PAK C18(UG) 4.6 mm i.d.×150 mm at a detection wavelength of 330 nm with a mobile phase consisting of 0.1% aqueous trifluoroacetic acid:0.1% trifluoroacetic acid 50% acetonitrile in water 85:15 at a flow rate of 1.0 ml/min to show that the hyperoside content was 2.1% and the isoquercitrin content was 2.7%.

The contents of hyperforin and hypericin in the above solid were determined by using a high performance liquid chromatograph (Von J. Holzl and E. Ostrowski, Deutche Apotecker Zeit. 127, 1227–30 (1987)) on a column YMC PAK ODS 100×6 mm i.d. with a mobile phase consisting of acetonitrile:methanol:water:phosphoric acid=55: 45:1:0.1 at 1 mL/min. A hyperforin peak appears at 8.9 min as monitored at a detection wavelength of 254 nm and a hypericin peak appears at 14.3 min as monitored at a wavelength of 590 nm, but the above solid showed no peak corresponding to hypericin and hyperforin during analysis by this method.

Example 3

Antidepressant Effect of Apocynum Extract (Acute Administration)

A common method for evaluating antidepressant effect called as the forced swimming test (Porsolt et al., Nature. 266, 730–732, (1977)) was used as follows. Male CD rats (230–250 g) were used in the tests. Forty animals were divided into groups of 8 animals treated with 30 mg/kg imipramine, 125 mg/kg, 250 mg/kg and 500 mg/kg Apocynum extract and purified water. Test solutions were orally administered 24 h, 5 h and 1 h before testing. Rats were forced to swim for 15 min in a Plexiglas cylinder (40×18 cm i.d.) containing water at 25° C. at a level of 17 cm so that they preliminarily learned that they could not escape from the cylinder. One hour after the final administration, the rats were forced to swim for 5 min, during which their action was recorded with a video camera and the total inactive period was calculated. All the tests were performed between 1–3 p.m. The images in the tapes were evaluated by a person who was not aware of the treatment of each group.

Test solutions were prepared by dissolving or suspending Apocynum extract prepared in Example 2 in purified water or dissolving imipramine-HCl (imipramine is a known tricyclic antidepressant) in purified water, and administered at a dose of 10 ml/kg body weight. The results from 8 experimental animals in each group were expressed in mean "SEM. Statistic significance as compared with control group was determined by ANOVA and multiple comparison tests were made by Fisher-PLSD (p<0.05:*). As apparent from the results shown in Table 1, the inactive period was significantly shortened in the group treated with 125 mg/kg Apocynum extract and the group treated with 30 mg/kg imipramine as compared with control group.

TABLE 1

| Test material | Inactive period (seconds) |
| --- | --- |
| Control | 209 ± 20 |
| Apocynum extract 500 mg/kg | 162 ± 23 |
| Apocynum extract 250 mg/kg | 192 ± 28 |
| Apocynum extract 125 mg/kg | 112 ± 29* |
| Imipramine 30 mg/kg | 137 ± 18* |

Example 4

Antidepressant Effect (Repeated Administration)

A common method for evaluating antidepressant effect called as the forced swimming test (Porsolt et al., Nature. 266, 730–732, (1977)) was used in the same manner as in Example 3. Male CD rats (230–250 g) were used in the tests. Forty animals were divided into groups of 8 animals treated with 20 mg/kg imipramine, 30 mg/kg, 60 mg/kg and 125 mg/kg Apocynum extract and purified water. Test solutions were orally administered between 3–4 p.m. daily. Rats were forced to swim for 15 min in a Plexiglas cylinder (40×18 cm i.d.) containing water at 25° C. at a level of 17 cm so that they preliminarily learned that they could not escape from the cylinder. One hour after the final administration, the rats were forced to swim for 5 min, during which their action was recorded with a video camera and the total inactive period was calculated. All the tests were performed between 1–3 p.m. The images in the tapes were evaluated by a person who was not aware of the treatment of each group.

Test solutions were prepared by dissolving or suspending Apocynum extract prepared in Example 2 in purified water or dissolving imipramine-HCl (imipramine is a known tricyclic antidepressant) in purified water, and administered at a dose of 10 ml/kg body weight. The results from 8 experimental animals in each group were expressed in mean±SEM. Statistic significance as compared with control group was determined by ANOVA and multiple comparison tests were made by Fisher-PLSD (p<0.05:*). As apparent from the results shown in Table 2, the inactive period was significantly shortened in the groups treated with 30 mg/kg and 125 mg/kg Apocynum extract and the group treated with 20 mg/kg imipramine as compared with control group.

TABLE 2

| Test material | Inactive period (seconds) |
| --- | --- |
| Control | 161.54 ± 16.5 |
| Apocynum extract 125 mg/kg | 123.5 ± 15.5* |
| Apocynum extract 60 mg/kg | 132 ± 10.7 |
| Apocynum extract 30 mg/kg | 121 ± 11.5* |
| Imipramine 20 mg/kg | 97.91 ± 9.6* |

Example 5

Preparation Example

Lactose and Apocynum extract prepared in Example 2 in the amounts shown in Table 3 were thoroughly mixed. This mixture was filled into gelatin capsules to prepare capsule formulations.

TABLE 3

| Component | Parts by weight |
| --- | --- |
| Apocynum extract of the present invention | 200 |
| Lactose | 50 |

Example 6

Preparation Example

Lactose, Apocynum extract prepared in Example 2 and a Siberian ginseng extract in the amounts shown in Table 4 were thoroughly mixed. This mixture was directly compressed into round tablets having a diameter of 8 mm by a tabletting machine.

TABLE 4

| Component | Parts by weight |
| --- | --- |
| Apocynum extract of the present invention | 200 |
| Siberian ginseng extract | 100 |
| Lactose | 50 |

Example 7

Preparation Example

Lactose, Apocynum extract prepared in Example 2 and a black cohosh extract in the amounts shown in Table 5 were thoroughly mixed, and this mixture was directly compressed into triangular tablets by a tabletting machine.

TABLE 5

| Component | Parts by weight |
| --- | --- |
| Apocynum extract of the present invention | 200 |
| Black cohosh extract | 20 |
| Lactose | 80 |

Example 8

Preparation Example

Lactose, Apocynum extract prepared in Example 2 and a soybean extract in the amounts shown in Table 6 were thoroughly mixed, and this mixture was filled into gelatin capsules to prepare capsule formulations.

TABLE 6

| Component | Parts by weight |
| --- | --- |
| Apocynum extract of the present invention | 200 |
| Soybean extract | 100 |
| Lactose | 50 |

INDUSTRIAL APPLICABILITY

The present invention provides Apocynum extracts characterized by containing not less than 4% of flavonoid compounds. The present Apocynum extracts exhibit an antidepressant effect and are useful as ingredients of antidepressants. The present Apocynum extracts can be used in compositions in the form of foods, dietary supplements, medicines and the like for improving depression symptoms.

What is claimed is:

1. An *Apocynum venetum* extract containing not less than 4% of flavonoid compounds and is free of hypericin and hyperforin.

2. The *Apocynum venetum* extract according to claim 1 containing not less than 4% of flavonoid compounds as expressed in a total content of hyperoside and isoquercitrin.

3. The *Apocynum venetum* extract according to claim 1 containing not less than 4% of flavonoid compounds as expressed in a total content of hyperoside, isoquercitrin, astragalin and trifolin.

4. The *Apocynum venetum* extract according to any one of claims 1 to 3, which is obtained from dried or roasted leaves of *Apocynum venetum* L.

5. An antidepressant composition containing the *Apocynum venetum* extract of claim 1.

6. The composition according to claim 5 in the form of a food, dietary supplement or medicine.

7. A method for treating depression, comprising:

administering to a patient in need thereof an effective amount of the *Apocynum venetum* extract of claim 1 or a composition containing said *Apocynum venetum* extract.

8. The method according to claim 7 wherein the composition is in the form of a food, dietary supplement or medicine.

\* \* \* \* \*